US00PP35368P2

(12) United States Plant Patent
Clark

(10) Patent No.: US PP35,368 P2
(45) Date of Patent: Sep. 5, 2023

(54) BLACKBERRY PLANT NAMED 'APF-404T'

(50) Latin Name: ***Rubus* subgenus *Rubus* Watson**
Varietal Denomination: APF-404T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/968,508

(22) Filed: Oct. 18, 2022

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark |
| PP11,865 | P2 | 5/2001 | Clark |
| PP14,935 | P2 | 6/2004 | Clark |
| PP15,788 | P2 | 6/2005 | Clark |
| PP16,989 | P3 | 8/2006 | Clark |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz |
| PP26,405 | P3 | 2/2016 | Clark |
| PP26,413 | P3 | 2/2016 | Ortiz |
| PP26,990 | P3 | 8/2016 | Clark |
| PP27,032 | P2 | 8/2016 | Clark |
| PP27,401 | P3 | 11/2016 | Clark |
| PP28,598 | P3 | 11/2017 | Clark |
| PP34,867 | P2 | 12/2022 | Clark |

OTHER PUBLICATIONS

Clark, J.R. et al., "'APF-45' primocane-fruiting blackberry," (2011) Hort. Science 46(4):670-673.
Ruple, A. et al., "An evaluation of fertility in Arkansas primocane-fruiting blackberries," (2010) Hort. Science 45:1-6.
Daugovish, O., et al. "Blackberry and Raspberry Cultivar Evaluations in Coastal California." HortTechnology 31.4 (2021): 552-558.

*Primary Examiner* — Susan McCormick Ewoldt
(74) *Attorney, Agent, or Firm* — Quarles & Brady LLP

(57) ABSTRACT

Description and specifications of a new and distinct cultivar of blackberry plant named 'APF-404T' which originated from seed produced by a hand-pollinated cross of Arkansas selections 'APF-185T' (a non-patented, unreleased breeding selection) x 'A-2444T' (a non-patented, unreleased breeding selection) is provided. This new cultivar of blackberry plant can be distinguished by its thornless canes, primocane-fruiting tendency, and large, sweet fruit. The plants have consistently good plant health and produce fruit suitable for home gardens.

4 Drawing Sheets

Latin name: *Rubus* subgenus *Rubus* Watson.
Varietal denomination: 'APF-404T'.

BACKGROUND

The new primocane-fruiting blackberry plant called 'APF-404T' is described herein. The new plant originated from a hand-pollinated cross of the unreleased Arkansas selections 'APF-185T' (female parent, a non-patented, unreleased breeding selection) x 'A-2444T' (male parent, a non-patented, unreleased breeding selection) made in 2011. The seeds resulting from this controlled hybridization were germinated in a greenhouse in the spring of 2012 and planted in a field near Clarksville, Ark. (West-Central Arkansas). The seedlings fruited in the summer of 2014 and one seedling, designated 'APF-404T' was selected. It was selected for having thornless canes, primocane-fruiting tendency, and large fruit with good flavor.

SUMMARY OF THE INVENTION

The new and distinct cultivar of blackberry originated from a hand-pollinated cross of Arkansas selections 'APF-185T' (a non-patented, unreleased breeding selection) x 'A-2444T' (a non-patented, unreleased breeding selection) made in 2011. The botanical designation of the new cultivar of blackberry is *Rubus* L. subgenus *Rubus* Watson. The seeds resulting from this controlled hybridization were germinated in a greenhouse in the winter to early spring of 2012 and planted in a field near Clarksville, Ark. The seedlings fruited in the summer of 2014 on floricanes and one seedling, designated 'APF-404T', was selected for its thornless canes, primocane-fruiting tendency, and large fruit with good flavor. During winter 2014-15, the original plant selection was propagated asexually from root cuttings at the above-noted location, and a test row of 10 plants were established.

The new cultivar has been asexually multiplied since 2014 by rooting adventitious shoots from root cuttings at the above-mentioned location. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants shown in the figures were three years old at the time of the photographs.

DETAILED DESCRIPTION OF THE NEW CULTIVAR 'APF-404T'

Figure 1:
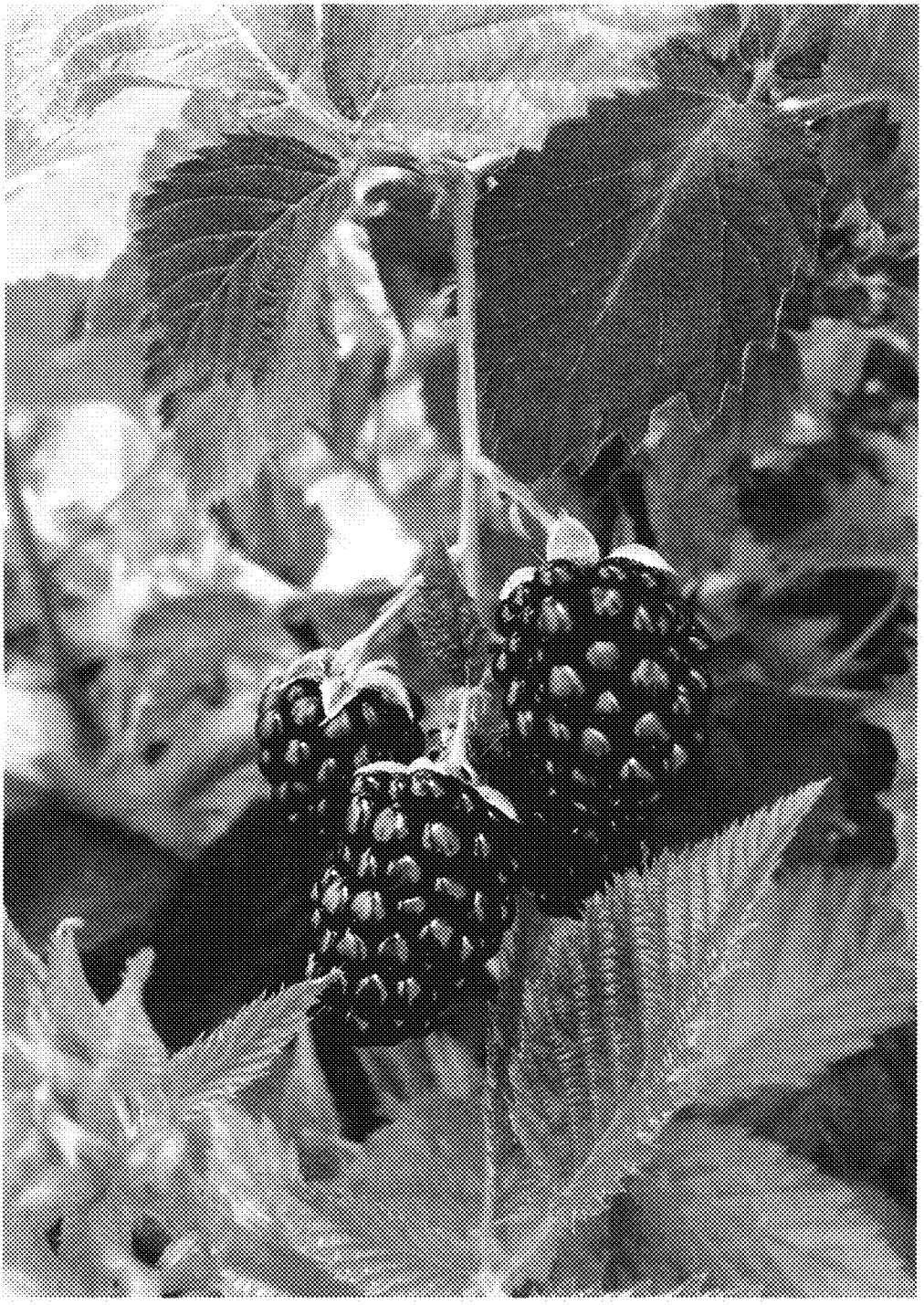
FIG. 1 is a photograph of fruits of 'APF-404T' borne on a floricane in mid-June, near Clarksville, Ark.
Figure 2:
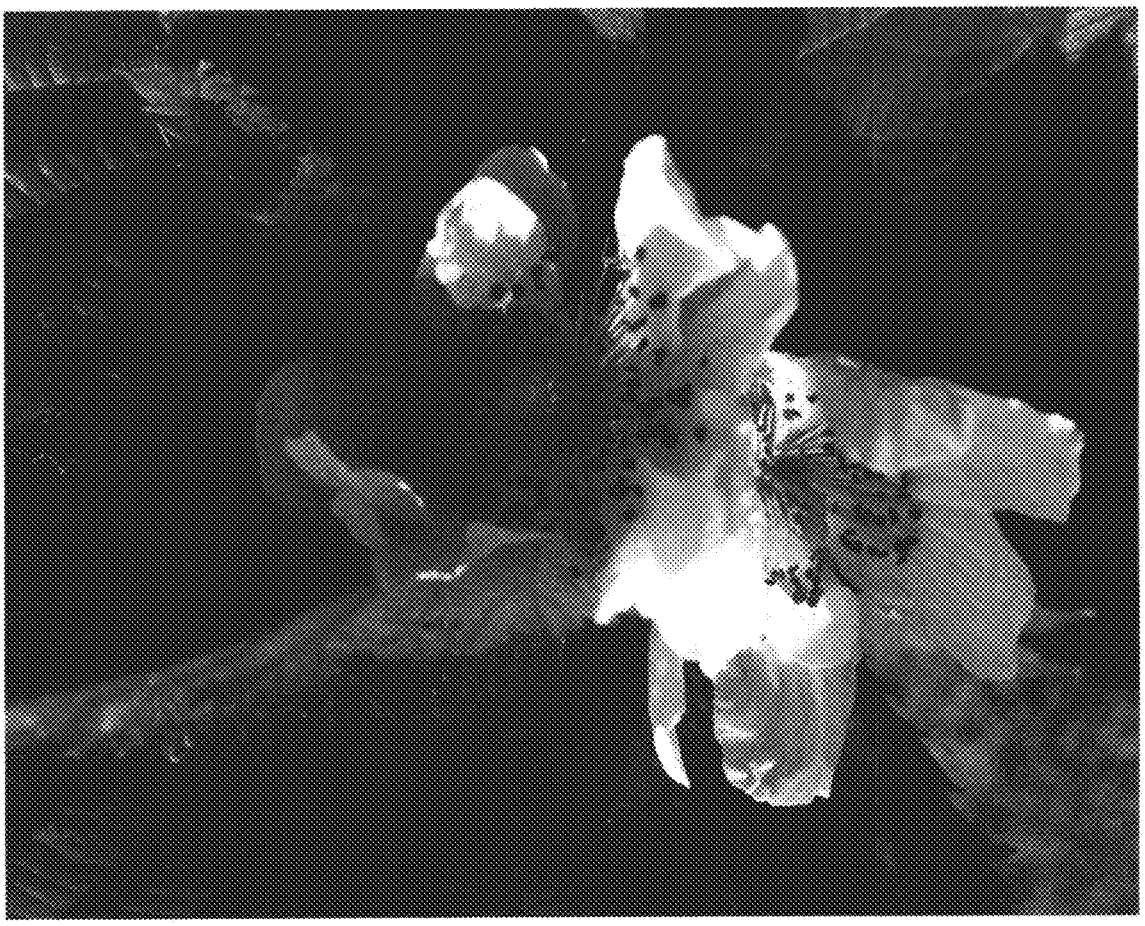
FIG. 2 is a photograph of primocane flowers of 'APF-404T', near Clarksville, Ark.
Figure 3:
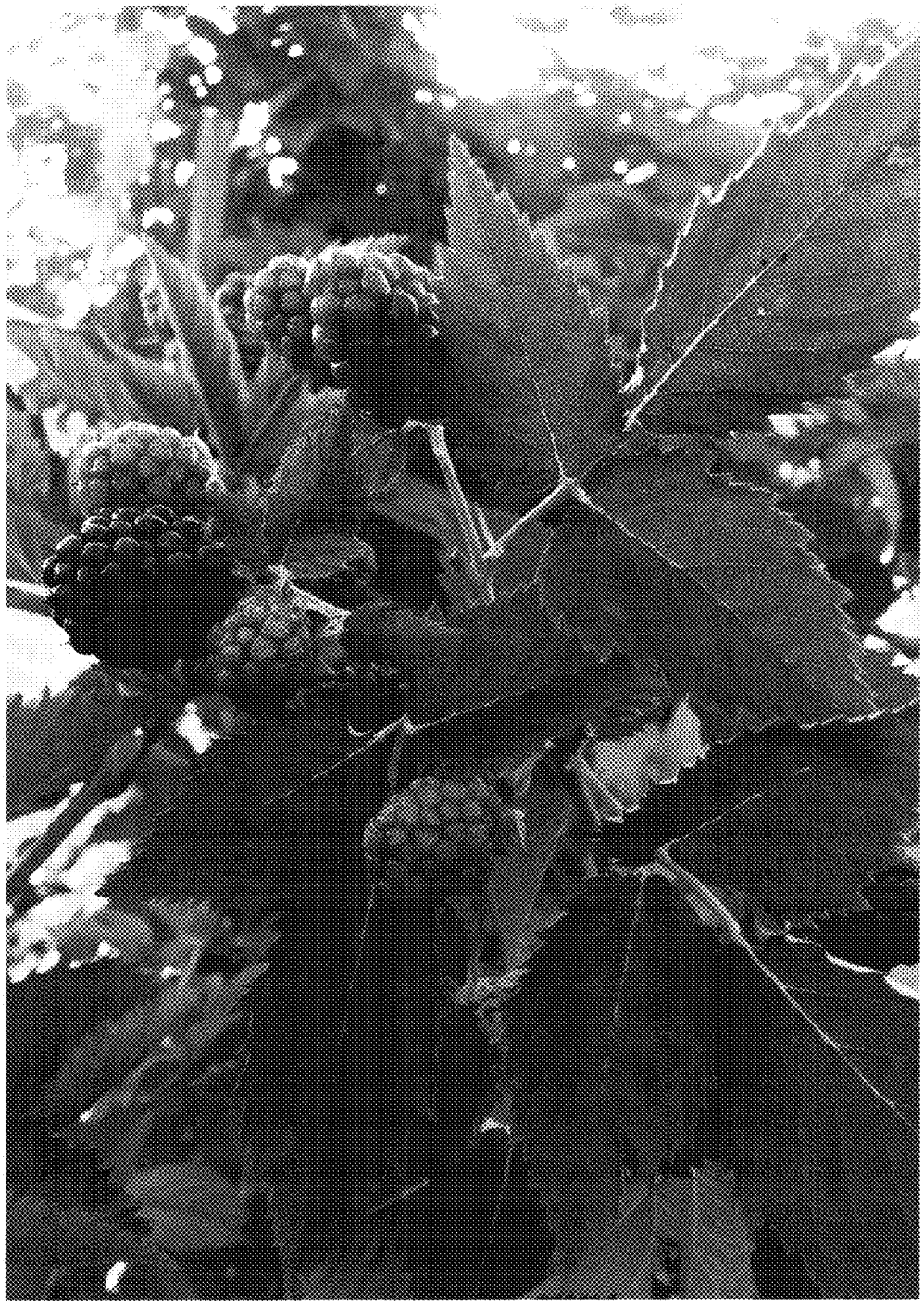
FIG. 3 is a photograph of primocane fruit of 'APF-404T', near Clarksville, Ark.
Figure 4:
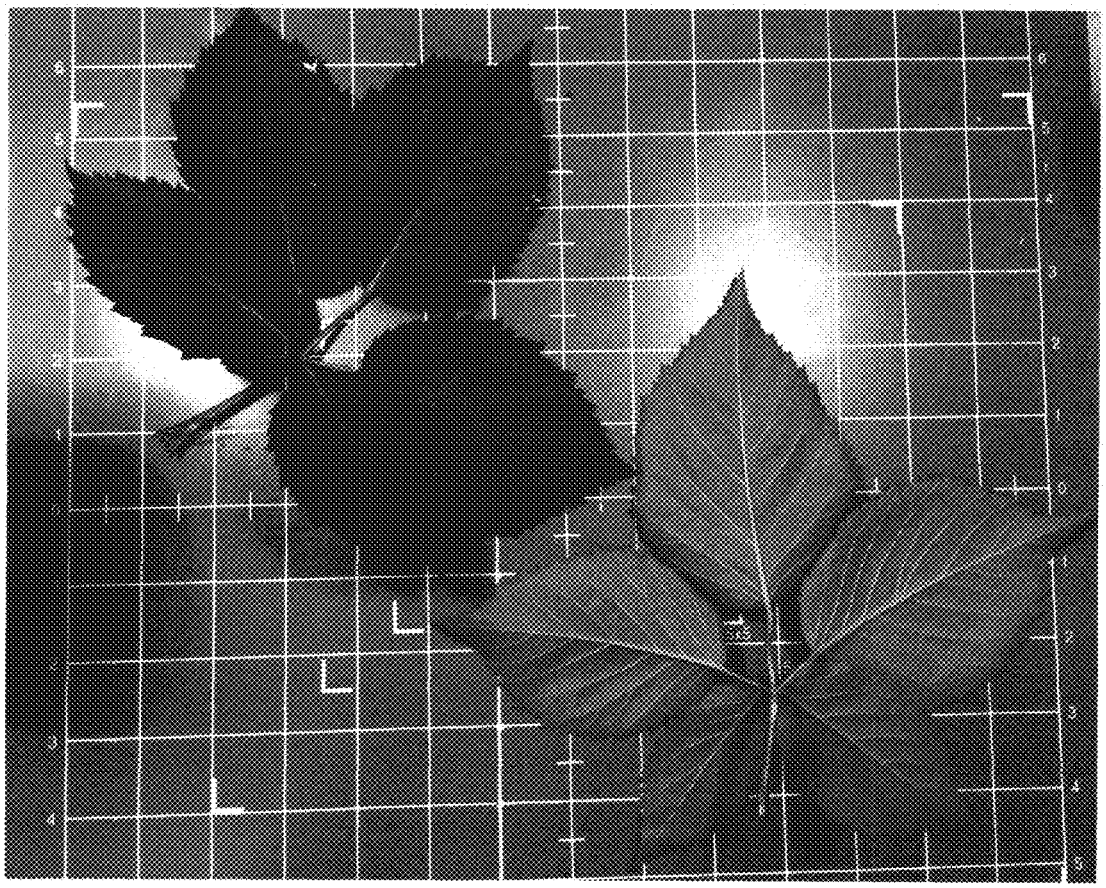
FIG. 4 is a photograph showing the abaxial (right) and adaxial (left) surfaces of primocane leaves of 'APF-404T', near Clarksville, Ark.

Plants and fruit of this new cultivar differ phenotypically from its parents. The new blackberry plant has 27% larger fruit (7.1 g) than 'APF-185T' (5.2 g) (female parent). Fruit from the new blackberry plant has improved flavor over the female parent, ranking an average of 1.0 point higher on a 1-10 rating scale used in annual breeder evaluations, with 10 being exceptionally good flavor. 'APF-404T' shares exceptional plant health and similar cropping potential with its female parent. In contrast to the male parent, 'A-2444T', 'APF-404T' produces fruit on primocanes. Although blackberries (*Rubus* L. subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes are best managed if trained to a hedgerow and a trellis with supporting wires used to prevent canes from falling over due to wind or heavy fruit loads. The plants are thornless and maintain good health throughout the growing season. Plants and fruit have not been noted to be affected by anthracnose [*Elsinoe veneta* (Burkh.) Jenkins], and plants have shown no evidence of susceptibility to orange rust [*Gymnoconia nitens* (Schwein.) F. Kern and H. W. Thurston.]. No screening has been done for resistance to double blossom/rosette [*Cercosporella rubi* (Wint.) Plakidas].

The new cultivar averages 50% of floricane blooms open on 3 May, 6 days earlier than 'APF-190T' (U.S. Plant Pat. No. 28,598) and 5 days before 'Ouachita' (U.S. Plant Pat. No. 17,162). Floricane fruit of the new cultivar has a harvest period of 37 days. Floricane fruit of 'APF-404T' has an average first ripe date of 4 June, similar to 'APF-190T' and 7 days earlier than 'Ouachita'. Primocane first ripe fruit date averages 15 July, 5-7 days earlier than 'APF-190T' on tipped primocanes. Primocane fruit development is dependent on environmental conditions, most importantly temperatures being below 32° C. (90° F.) to allow fruiting. In Clarksville, Ark., the primocane-fruit harvest period can extend into early fall.

Fruit yield of the new cultivar has not been evaluated with objective measurements, as this new plant is intended for the home gardening market. However, 'APF-404T' has been consistently rated to have good productivity.

The fresh fruit rates good in flavor, comparable to comparison cultivars. The soluble solids concentration averages 12.2% on floricane fruit and 12.6% on primocane fruit for 'APF-404T'. In comparison, soluble solids content on 'APF-190T' averages 11.4% on floricane fruit and 12.4% for primocane fruit.

Primocane fruit and flowers are borne on the cane terminus or on lateral branches if primocanes are tipped, and fruiting continues down the primocane during the season. Canes usually attain a length of 1.5 to 1.8 m (4-5 ft) prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (February to March) with complete or nitrogen fertilizer and had an additional nitrogen fertilizer application in early July. Primocanes were tipped at approximately 1.14 m (45 inches) and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

- *Size*.—Medium. Plants are grown in a hedgerow and primocanes tipped at approx. 114 cm; plants in this system range in size from approx. 135-140 cm tall and 91-102 cm wide.
- *Growth habit*.—Moderate vigor, canes erect; suckers primarily from the crown of the plant.
- *Growth rate*.—First emergence of primocanes is 23 March and primocanes reach tipping height (114 cm) approximately 22 May.

Productivity:

- *Floricane*.—Yield was not evaluated, as this cultivar is intended for home-garden use.
- *Primocane*.—Yield was not evaluated, as this cultivar is intended for home-garden use.
- *Cold hardiness*.—Hardy to −17° C. (1° F.).
- *Canes*.—Thornless, erect.
- *Disease resistance*.—Moderate resistance to anthracnose, and no evidence of orange rust disease. No screening has been done for resistance to double blossom/rosette.

Floricane (dormant or winter cane):

- *Cane diameter*.—Base: 1.55 cm; midpoint: 1.22 cm; terminus: 0.87 cm.
- *Internode length*.—Base: 5.48 cm; midpoint: 6.08 cm; terminus: 3.29 cm.

*Floricane color*.—Base: greyed-purple group (187A) on sun-exposed side, green group (143C) on shaded side; midpoint: greyed-purple group (185A) on sun-exposed side, yellow-green group (144B) on shaded side; terminus: greyed-purple group (185A) on sun-exposed side, yellow-green group (152D) on shaded side.

*Thorn density/30 cm*.—Not applicable; this plant is thornless.

*Thorn size*.—Not applicable; this plant is thornless.

*Thorn color*.—Not applicable; this plant is thornless.

*Lateral branching after tipping* (*measured at the end of growing season*).—Average number of lateral branches: 2; distribution: top half of the canes; anthocyanin present: yes; color: greyed-orange group (166A) and greyed-purple group (187A).

*Shape of dormant cane cross-section*.—Round near base and midpoint, gradually getting more angular near the terminus.

Primocane (current-season cane):

*Date of primocane emergence*.—23 March.

*Number of new canes per season*.—5.

*Cane diameter*.—Base: 1.34 cm; midpoint: 10.41 cm; terminus: 0.69 cm.

*Internode length*.—Base: 8.27 cm; midpoint: 5.83 cm; terminus: 3.14 cm.

*Primocane color*.—Base: green group 137C; midpoint: green group 144A; terminus: green group (144C). No anthocyanin coloration present on primocanes.

*Thorn density/30 cm*.—Not applicable; this plant is thornless.

*Thorn size*.—Not applicable; this plant is thornless.

*Thorn color*.—Not applicable; this plant is thornless.

*Lateral branching after tipping* (*measured at the end of growing season*).—Average number of lateral branches: 7; distribution: predominantly on the distal one-third of the canes.

*Relative number of glandular hairs on young shoot*.—Absent or few.

Foliage (floricane):

*Leaves*.—Shape: compound palmate; size: width: 15.06 cm; length: 12.28 cm; budbreak: 4 February.

*Glossiness*.—Abaxial: dull; adaxial: low, slight sheen.

*Leaflet*.—Width: 7.18 cm; length: 8.54 cm; overall shape: ovate; leaflet shape in cross section: v-shaped; degree of undulation on terminal leaflet: moderate undulation; degree of blistering on terminal leaflet: none; leaflet margin: biserrate; serration teeth length: 3.15 mm; width at base of teeth: 4.18 mm; pubescence: abaxial: heavy; adaxial: light.

*Number of leaflets per compound leaf*.—3.

*Leaf color*.—Base: abaxial: yellow-green group (146B), adaxial: green group (137A); midpoint: abaxial: yellow-green group (146B), adaxial: green group (137A); terminus: abaxial: yellow-green group (146B), adaxial: green group (137A).

*Petioles*.—Length: 4.78 cm; diameter: 1.98 mm; color: yellow-green group (144A); texture: heavy pubescence.

*Petiolules*.—Length: 1.31 cm; diameter: 1.46 mm; color: yellow-green group (144A); texture: light pubescence.

*Stipules*.—Number present: 2; length: 0.89 cm; width: 1.91 mm; shape: overall: linear; apex: acute; margin: smooth; base: cuneate; texture: abaxial: moderate pubescence; adaxial: no pubescence, smooth.; color: abaxial: yellow-green group (146A); adaxial: green group (141B).

*Venation*.—Pattern: pinnate; vein color (mature leaves): abaxial: yellow-green group (145A); adaxial: yellow-green group (144A); vein color (young leaves): abaxial: yellow-green group (145A); adaxial: yellow-green group (144A).

Foliage (primocane):

*Leaves*.—Shape: compound palmate; size: width: 22.28 cm; length: 19.60 cm.

*Glossiness*.—Abaxial: none, dull; adaxial: low, slight sheen.

*Leaflet*.—Width: 9.06 cm; length: 11.70 cm; overall shape: acuminate; shape in cross section: v-shaped; degree of undulation on terminal leaflet: moderate undulation; degree of blistering on terminal leaflet: none; leaflet margin: biserrate; serration teeth length: 2.60 mm; width at base of teeth: 1.99 mm; pubescence: abaxial: heavy pubescence; adaxial: light pubescence.

*Number of leaflets per compound leaf*.—5.

*Leaf color*.—Base: abaxial: green group (137A), adaxial: yellow-green group (146B); midpoint: abaxial: green group (137A), adaxial: yellow-green group (146B); terminus: abaxial: green group (137A), adaxial: yellow-green group (146B).

*Petioles*.—Length: 3.19 cm; diameter: 3.10 mm color: yellow-green group (146C); texture: light pubescence.

*Petiolules*.—Length: 2.27 cm; diameter: 2.07 mm; color: yellow-green group (144A); texture: light pubescence.

*Stipules*.—Number present: 2; length: 1.41 cm; width: 1.15 mm; shape: overall: subulate; apex: acuminate; margin: smooth; base: cuneate; texture: abaxial: moderate to heavy pubescence; adaxial: moderate pubescence.; color: abaxial: yellow-green group (144A); adaxial: yellow-green group (144B).

*Venation*.—Pattern: pinnate; vein color (mature leaves): abaxial: yellow-green group (145A); adaxial: yellow-green group (144B); vein color (young leaves): abaxial: yellow-green group (145A); adaxial: yellow-green group (144B).

Flowers (floricane):

*Date of first bloom*.—First bloom averages 12 April, 50% bloom averages 3 May.

*Petal color*.—Abaxial: white group (155D); adaxial: white group (155D).

Reproductive organs:

*Stamens*.—Numerous.

*Pistils*.—Numerous.

*Pollen*.—Normal, fertile, and abundant.

*Flower*.—Size: diameter: 4.23 cm; depth: 1.47 cm; shape: overall: rotate; symmetry: actinomorphic.

*Petal size*.—Length 1.93 cm; width 1.37 cm.

*Petal shape*.—Overall: medium elliptic; apex: obovate; margin: sinuate; base: acuminate.

*Petal texture*.—Abaxial: light pubescence; adaxial; no pubescence.

*Average number flowers per cluster*.—3.

*Average number of petals per flower*.—9.

*Sepals*.—Length 0.80 cm; width: 0.47 cm; shape: overall: aristate; apex: aristate; margin: smooth (entire); base: truncate; texture: abaxial: light pubescence;

adaxial: no pubescence; color: abaxial: yellow-green group (144A); adaxial: yellow-green group (144B); number per flower: 5.

*Pedicel*.—Length: 3.14 cm; diameter: 0.93 mm; color: yellow-green group (146A); texture: moderate pubescence.

*Peduncle*.—Size: length: 1.16 cm; width: 5.25 mm; color: yellow-green group (144B).

*Cyme type*.—Simple cyme; length: 13.40 cm.

Flowers (primocane):

*Date of bloom*.—First bloom: 12 June and can extend until frost depending on environment and cultural management.

*Petal color*.—Abaxial: white group (155D); adaxial: white group (155D).

Reproductive organs:

*Stamens*.—Numerous.

*Pistils*.—Numerous.

*Pollen*.—Fertile and abundant unless temperatures exceed 32° C. (90° F.) at which temperature can damage flowers and anthers and pollen production can be reduced.

*Flower*.—Size: diameter: 2.86 cm; depth: 1.93 cm; shape: overall: rotate; symmetry: actinomorphic.

*Petal size*.—Length: 1.97 cm; width: 1.07 cm.

*Petal shape*.—Overall: medium elliptic; apex: obovate; margin: sinuate; base: acuminate.

*Petal texture*.—Abaxial: light pubescence; adaxial: no pubescence.

*Average number flowers per cluster*.—2.

*Average number of petals per flower*.—8.

*Sepals*.—Length 1.9 cm; width: 0.42 cm; shape: overall: aristate; apex: aristate; margin: smooth (entire); base: truncate; texture: abaxial: light pubescence; adaxial: no pubescence; color: abaxial: yellow-green group (144A); adaxial: yellow-green group (144B); number per flower: 6.

*Pedicel*.—Length: 3.68 cm; diameter: 2.02 mm; color: yellow-green group (146B); texture: moderate pubescence.

*Peduncle*.—Size: length: 1.78 cm; width: 10.96 mm; color: yellow-green group (146C).

*Cyme type*.—Elongated compound cyme; length: 27.86 cm.

Fruit (floricane):

*Maturity*.—Average first ripe date 4 June.

*Size*.—Large, average 7.1 g.

*Diameter of fruit at primary position on inflorescence*.—Equator: 2.32 cm; base pole: 2.03 cm; terminus pole: 10.34 cm.

*Diameter of fruit at secondary positions on inflorescence*.—Equator: 2.18 cm; base pole: 1.94 cm; terminus pole: 1.24 cm.

*Length* (*primary fruit*).—3.07 cm.

*Length* (*secondary fruit*).—2.73 cm.

*Length* (*tertiary fruit*).—3.10 cm.

*Shape*.—Narrow ovate.

*Color*.—Black group (202A).

*Drupelet size*.—Length: 6.74 mm; width: 4.96 mm.

*Drupelets per berry*.—88.

*Seed size*.—Length: 3.89 mm; width: 2.40 mm.

*Seed weight*.—Wet: 32.70 mg; dry: 6.2 mg.

*Seed color*.—Wet: red-purple group (59B); dry: red-purple group (60B).

*Soluble solids*.—12.2%.

*PH*.—4.02.

*Titratable acidity*.—0.71% citric acid.

*Processed quality*.—Not evaluated for processing.

*Uses*.—For home garden, local fresh-market, or commercial shipping.

Fruit (primocane):

*Maturity*.—Average first ripe date 15 July on tipped primocanes and can fruit until frost depending on environment and cultural management.

*Size*.—5.9 g/berry.

*Diameter of fruit at primary position on inflorescence*.—Equator: 2.26 cm; base pole: 2.45 cm; terminus pole: 1.64 cm.

*Diameter of fruit at secondary positions on inflorescence*.—Equator: 2.12 cm; base pole: 2.20 cm; terminus pole: 1.28 cm.

*Length* (*primary fruit*).—3.18 cm.

*Length* (*secondary fruit*).—3.27 cm.

*Length* (*tertiary fruit*).—2.80 cm.

*Shape*.—Narrow ovate.

*Color*.—Black group 202A.

*Drupelet size*.—Length: 6.88 mm; width: 6.13.

*Drupelets per berry*.—75.

*Seed size*.—Length: 4.02 mm; width: 2.20 mm.

*Seed weight*.—Wet: 27.5 mg; dry: 5.2 mg.

*Seed color*.—Wet: red-purple group (60A); dry: red-purple group (60C).

*Soluble solids*.—12.6%.

*PH*.—4.37.

*Titratable acidity*.—0.62% citric acid.

*Processed quality*.—Not evaluated for processing.

*Uses*.—For home garden. This variety is not intended for commercial shipping and does not store well for long periods of time.

The cultivar: The most distinctive features of the new cultivar of blackberry plant are thornless canes, primocane-fruiting tendency, and large fruit with good flavor.

I claim:

1. A new and distinct cultivar of blackberry plant named 'APF-404T', substantially as illustrated and described.

* * * * *